United States Patent [19]

Beilfuss et al.

[11] Patent Number: 5,387,605
[45] Date of Patent: Feb. 7, 1995

[54] CARBOXYLIC ACIDS THAT ARE EFFECTIVE AGAINST TB

[75] Inventors: Wolfgang Beilfuss, Hamburg; Karl-Heinz Diehl, Norderstedt; Heinz Eggensperger, Hamburg; Michael Mohr, Kaltenkirchen, all of Germany

[73] Assignee: Eastman Kodak Company, Rochester, N.Y.

[21] Appl. No.: 69,249

[22] Filed: May 28, 1993

[30] Foreign Application Priority Data

Jul. 31, 1992 [DE] Germany .............................. 4225794

[51] Int. Cl.⁶ ...................... A01N 43/08; A01N 37/10
[52] U.S. Cl. ...................................... 514/461; 514/568
[58] Field of Search ......................................... 514/461

[56] References Cited

PUBLICATIONS

Chemical Abstracts 100:137721p (1984) and Chemical Abstracts formula Index p. 220F, col. 1 under 2-Furancarboxylic acid P-137721p (1984).

*Primary Examiner*—Jerome D. Goldberg
*Attorney, Agent, or Firm*—John R. Everett

[57] ABSTRACT

The use of carboxylic acids for controlling mycobacteria is described. The carboxylic acids contain compounds with the general formula:

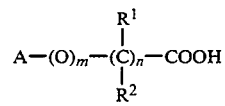

in which
  A is a substituted or unsubstituted $C_5$-$C_{10}$ aryl group, A containing no nitrogen atom,
  $R^1$ and $R^2$ each independently of one other are hydrogen or a $C_1$-$C_3$ alkyl group,
  m is 0 or 1 and
  n is a number from 0 to 5, and no alkyl sulphonates or alkyl sulphates are present.

Said active ingredients may be used in the form of aqueous and/or alcoholic ready-for-use solutions or may be present in the form of concentrates, powders or granular products or applied to a support such as a cloth. Formulations based on said carboxylic acids may also contain other bactericidal active ingredients, synergistic effects arising in some cases.

10 Claims, No Drawings

CARBOXYLIC ACIDS THAT ARE EFFECTIVE AGAINST TB

The invention relates to the use of carboxylic acids as bactericidal active ingredients.

Disinfectants with bactericidal active ingredients are used in many spheres where they serve to combat microorganisms. For example, they are used for the disinfection of hands, operating areas, wounds, instruments, surfaces, laundry, in the field of agriculture, disaster control and plant protection.

The efficacy of disinfectants against mycobacteria is of great interest, particularly against tuberculosis pathogens which, because of their structural composition, are comparatively resistant in relation to bacteria or fungi and yeasts with the result that frequently no destruction takes place; their multiplication is merely inhibited for a short period. As short as possible contact times of the disinfectants with a none the less thorough and lasting disinfectant effect are desirable.

Amongst others, aldehydes such as formaldehyde, succinaldehyde or glutaraldehyde, phenol compounds, active oxygen compounds such as peracetic acid, amine compounds such as N,N-bis (3aminopropyl) laurylamine, alcohols such as ethanol, isopropanol, n-propanol or phenoxyethanol are known as active ingredients against mycobacteria. These are predominantly lipophilic, volatile, reactive substances or substances giving an alkaline reaction that have a number of disadvantageous properties. For example, they are so sparingly soluble in water that the use of solvents or solubilizers is required, there are ecotoxicological concerns about their use as with the use of phenols for example, they lead to a considerable odour nuisance, for example, aldehydes, they have unsatisfactory stability, for example, active oxygen compounds such as peracetic acid, their volatility, their flash point and their flammability requires particular attention and care during handling, for example, lower alcohols, there is a possibility of the formation of nitrosamines as in the case of amines, for example, in view of their comparatively poor to moderate efficacy a high concentration in use is required as in the case of aromatic alcohols, or there is incompatibility with other constituents of the formulation as in the case of amines or aromatic alcohols, for example, which, if they are used together with cationic compounds, collect on surfaces and are deactivated by anionic surfactants.

Moreover, it is known from DE 32 29 097 that combinations of alkyl sulphonates and alkyl sulphates with carboxylic acids such as tartaric acid, lactic acid, benzoic acid, furan-2-carboxylic acid or pyridine carboxylic acid have an antibacterial and fungicidal effect. Efficacy of the individual components in relation to the particularly resistant mycobacteria is not described.

The invention is based on the task of providing active ingredients which have an excellent and rapid effect on mycobacteria yet are also sufficiently soluble, lacking in odour, non-volatile, sufficiently stable, environmentally compatible, readily biodegradable, very compatible with other constituents of the formulation, have a microbicidal effect over a broad range and are obtainable at a reasonable price.

As a means of achieving said aim, the use of carboxylic acids is proposed for combating mycobacteria, which acids are characterized in that they contain compounds having the general formula:

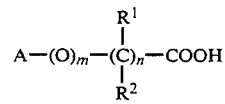

in which A is a substituted or unsubstituted $C_5$–$C_{10}$ aryl group containing no nitrogen atom, $R^1$ and $R^2$ each independently of one another are hydrogen or a $C_1$–$C_3$ alkyl group, m is 0 or 1 and n is a number from 0 to 5;

and provided that no alkyl sulphonates or alkyl sulphates are present.

Preferred embodiments are the subject of the subclaims.

Surprisingly, it has become apparent that the carboxylic acids according to the invention with limited solubility in water, both individually and in a combination of two or several of the same, exhibit excellent efficacy against mycobacteria and fulfill the desired requirement profile, in particular those carboxylic acids in which A is a $C_5$–$C_6$ aryl group, $R^1$ and $R^2$ are hydrogen and m and n each independently of one other are 0 or 1 having proved to be suitable.

Carboxylic acids with limited solubility in water are those that have a water solubility of <4% by wt. and preferably <3% by wt. at room temperature.

Preferred examples of carboxylic acids according to the invention are furan-2-carboxylic acid, phenoxyacetic acid, benzoic acid, pllenylacetic acid and salicylic acid. Of these, furan-2carboxylic acid and phenoxyacetic acid are particularly preferred.

The carboxylic acids according to the invention may be used either in their acid form or in the form of their salts, for example, their alkali metal salts. They may be converted from said salts into the more effective acid form by means of acidifying agents present in the finished formulation, for example, organic or inorganic acids or acid cleaning agents.

The carboxylic acids according to the invention which are effective against Tb may be present in the form of an aqueous and/or alcoholic ready-for-use solution, a liquid concentrate, powder or granular product or applied to supports, for example, cloths.

It is advantageous that the carboxylic acids according to the invention which are effective against Tb also have excellent stability in a liquid concentrate, powder or granular formulation or applied to a support, and in view of their sufficient solubility in water and/or alcohol an activated solution of active substance again with excellent storage stability may be prepared by simple dilution with, dissolution in or rinsing with water.

A ready-for-use solution has a pH of up to 7, more preferably up to 5 and in particular preference up to 4.

In order to achieve a sufficient disinfectant effect, the concentration of the carboxylic acids according to the invention or salts thereof, based on the total weight of the solution, is in the region of 0.01 to 8%, preferably 0.1 to 6%, more preferably 0.2 to 4% and in particular 0.5 to 2%.

Moreover, the formulations containing the carboxylic acids according to the invention may also be used in combination with auxiliaries, additives and/or other bactericidal active ingredients customary for the disinfectant sector. For example, alcohols, aldehydes, amines, ethers, cationic compounds, nonionic, anionic or amphoteric surfactants, anti-corrosion agents, perfume, dyes or complexing agents are suitable for this purpose, synergistic effects with the active ingredients arising in some cases, for example, in the combination with phenoxyethanol. Nonionic, amphoteric, cationic and anionic surfactants and alcohols are preferred, amphoteric, cationic and anionic surfactants and alcohols being particularly preferred.

As a result of the combination with other active ingredients, a broader spectrum of activity may be obtained, depending on the application. Combinable active ingredients which are compatible with the carboxylic acids according to the invention are, for example, aldehydes such as formaldehyde, succinaldeyde, glutaraldehyde or glyoxal, cationic compounds such as benzalkonium chloride, active oxygen compounds such as $H_2O_2$, peracetic acid, perglutaric acid or t-butyl hydroperoxide.

Another advantage of using the carboxylic acids according to the invention is that in view of their low volatility they have relatively little odour. Moreover, they are readily biodegradable and environmentally compatible.

Instead of water, alcohols may also be used as solvent or solubilizer for preparing concentrates or ready-for-use solutions. Suitable alcohols that in some cases themselves have a bactericidal effect are, for example, aliphatic alcohols with up to 16 carbon atoms (mono, di, tri or polyhydroxy compounds), aromatic alcohols with up to 10 carbon atoms, glycols and glycol ethers.

Examples of aliphatic alcohols are ethanol, n-propanol, i-propanol, 2-ethylhexanol, 2-ethylhexenol, n-decanol, tetrahydrofurfuryl alcohol, sorbitol and glycerol. Examples of aromatic alcohols are benzyl alcohol, 2-phenylethyl alcohol, α-methylbenzyl alcohol, phenylpropanols and phenylbutanols, where the compounds may be substituted on the aromatic ring or in the alkyl chain. Examples of glycols are ethylene glycol, propylene glycols, butylene glycols, diethylene glycol, triethylene glycol, tetraethylene glycol, polyethylene glycols, dipropylene glycol, diglycerol, triglycerol and polyglycerol. Examples of glycol ethers are phenoxyethanol, phenoxydiethylene glycol, phenoxytriethylene glycol, phenoxytetraethylene glycol, phenoxypolyethylene glycol, phenoxypropanols, phenoxybutanols, where the aromatic ring may also be substituted, butyl glycol, butyl diglycol, hexyl glycols, octyl glycols and decyl glycols. Preferred compounds are ethanol, i-propanol, n-propanol, phenoxyethanol, phenethyl alcohol, 3-phenylpropanol-1, phenoxybutanol and phenoxypropanol (the last two present as mixtures of isomers) and phenoxytetraethylene glycol (e.g., obtainable as a commercial product under the name Rewopal MPG 40). Ethanol, i-propanol and n-propanol are particularly preferred.

Nonionic surfactants such as fatty alcohol polyglycol ethers, anionic surfactants such as alkyl ether sulphates, for example, are suitable as surfactants or wetting agents, the surfactants also being able to contribute to foam regulation and to supporting the cleaning activity and the efficacy. Preferred disinfectants according to the invention also contain anionic surfactants such as fatty alkyl ether sulphates in addition to the carboxylic acids and alcohols.

Suitable complexing agents are, for example, ethylene diamine tetraacetic acid (EDTA), nitrilotriacetic acid (NTA) and dihydroxyethyl glycine or salts thereof which are also able to improve the biocidal effect.

Agents for correcting the pH such as inorganic or organic acids, bases or salts thereof may also be used together with the carboxylic acids according to the invention.

Generally, inert substances such as sodium sulfate and similar substances are suitable as fillers and supports.

Formulations containing the carboxylic acids according to the invention are stable in storage, have a high microbicidal efficacy and also have a broad spectrum of activity, as a result of which in particular the mycobacteria that are difficult to inactivate may be combated effectively as well as bacteria, yeasts and fungi.

In comparison with known disinfectants, formulations based on the carboxylic acids according to the invention have the following advantages in particular:

1. efficacy even at temperatures below 18° C.
2. no occurrence of foam problems,
3. excellent stability and storage stability,
4. low volatility of the active ingredients, little odour,
5. biodegradability and ability to be handled without danger,
6. excellent efficacy over a wide spectrum of activity with short contact times,
7. by increasing the pH, conversion to the corresponding less active salt solutions takes place, whilst by lowering the pH the original efficacy may be restored,
8. in some cases, an increased effect in combination with other auxiliaries, additives or active ingredients,
9. good to very good material compatibility,
10. support of the cleaning effect
11. economically and ecologically more effective use.

The expression stability in the present connection refers both to the appearance of the solutions (no precipitates, turbidity, inhomogeneities) and to the constancy of the pH and the constancy of the active ingredient contents.

Formulations based on the carboxylic acids according to the invention are suitable for treating surfaces, instruments, appliances, skin and hands. They may be used, for example, in hospitals, medical practices, public and private establishments such as baths, saunas, sports centers, hotels, households (bathroom, kitchen), industrial plants, particularly in the food processing industry, the cosmetic and pharmaceutical industry, inagriculture (animal keeping, plant breeding, horticulture), disaster control or plant protection.

In particular, the use instead of percarboxylic acids such as peracetic acid which are highly reactive, in some cases have a very intensive odour and only limited stability, is conceivable.

The invention will be explained in more detail on the basis of the following examples. Unless otherwise stated, all data relating to parts and percentages are based on weight.

EXAMPLE 1

For comparative purposes, the efficacy against mycobact. terrae of carboxylic acids that are not classed among the carboxylic acids according to the invention was tested in the instrument test according to Deutsche Geseeschaft fur Hygiene und Mikrobiologie (German association for Hygiene and Microbiology).

To this end, aqueous solutions of the carboxylic acids to be tested and test formulations were prepared with the active ingredient concentrations given in the table (2% active ingredient concentration means 2 parts by weight carboxylic acid +98 parts by weight water).

| Carboxylic Acid | Conc. of act. ingred | Solvent: Water Contact Time | | | |
|---|---|---|---|---|---|
| | | 15' | 30' | 45' | 60' |
| Lactic acid | 2% | ++++ | ++++ | +++ | +++ |
| | 1% | 8 | 8 | 8 | 8 |
| Malic acid | 2% | 8 | 8 | 8 | 8 |
| Tartaric acid | 2% | 8 | 8 | 8 | 8 |
| Glutaric acid | 2% | 8 | ++++ | +++ | +++ |
| | 1% | 8 | ++++ | ++++ | ++++ |

Legend: 8 = very substantial growth
++++ and +++ and ++ and +. M and E = substantial to sporadic growth in decreasing order.
− = no growth.

The carboxylic acids tested are practically ineffective against mycobacteria.

EXAMPLE 2

In this example, the efficacy against mycobacteria of carboxylic acids according to the invention was tested in the instrument test according to Deutsche Geseeschaft fur Hygiene und Mikrobiologie (German association for Hygiene and Microbiology).

Again, aqueous solutions of the active ingredients were prepared. Solvent: Water

| Carboxylic acid | Conc. of act. ingred | Solvent Water Contact Time | | | |
|---|---|---|---|---|---|
| | | 15' | 30' | 45' | 60' |
| Furan-2-carboxylic acid | 1% | − | − | − | − |
| | 0.5% | ++++ | E | − | − |
| | 0.25% | 8 | +++ | ++++ | +++ |
| Phenoxyacetic acid | 1.2% | + | − | − | − |
| Furan-2-carboxylic acid Na salt (pH7) | 4% | ++++ | ++++ | ++++ | ++++ |

Legend: 8 = very substantial growth,
++ and + and M and E substantial to sporadic growth in decreasing order, no growth.

The tests show that the carboxylic acids tested have an excellent effect against mycobact. terrae. They are significantly more effective than the carboxylic acids currently used in disinfectants and cleaning agents. At pH values of about 7, the efficacy is markedly reduced since in that case the less effective salt is present.

EXAMPLE 3

In this example, the efficacy against mycobacteria of the carboxylic acids according to the invention in combination with a cationic compound (benzalkonium chloride) was tested in the instrument test according to DGHM.

The formulation used was composed of two parts carboxylic acid and 10 parts benzalkonium chloride (50%) and 88 parts of fully demineralized water.

| Acid | Concentration in use | Contact Time | | | |
|---|---|---|---|---|---|
| | | 15' | 30' | 45' | 60' |
| 2 pts furan-2-c' acid +10 pts benzalkon +88 pts water | 50% | − | − | − | − |
| | 25% | M | − | − | − | pH values: conc.: 1.7; 1% in tap water 4.2; 10% in tap water 2.7

| 2 pts phosphoric ac. 75% (BRW) +10 pts benzalkon +88 pts water | conc. | + | M | M | E |
|---|---|---|---|---|---|
| | 50% | ++++ | +++ | +++ | +++ |
| | 25% | ++++ | +++ | +++ | +++ | pH values: conc.: 1.5; 1% in tap water 4.4; 10% in tap water 2.3

Legend: 8 = very substantial growth
++++ and +++ and ++ and + and M and E = substantial to sporadic growth in decreasing order,
− = no growth
BRW = industrial crude product
Concentration in use = amount of each formulation in the mixture with water.

The example shows that the combination of carboxylic acid according to the invention with other biocidal active ingredients such as benzalkonium chloride is as effective as before against Tb, whilst a combination with acids, for example, phosphoric acid does not develop any efficacy against Tb.

EXAMPLE 4

In this example, the efficacy against mycobact.terrae of a combination of carboxylic acid according to the invention with phenoxyethanol (another bactericidal active ingredient) was tested in the instrument test according to DGHM. The formulation used was composed of 10 parts carboxylic acid and 90 parts phenoxyethanol.

| Acid | Conc. in use | Contact Time | | | |
|---|---|---|---|---|---|
| | | 15' | 30' | 45' | 60' |
| 10 pts furan +90 pts phenyoxyethanol | 2% | − | − | − | − |
| | 1% | +++ | +++ | ++ | + |
| | 0.5% | ++++ | ++++ | ++++ | ++++ |
| For comparison: | | | | | |
| 0.2% furan-acid-c' acid | | ++++ | ++++ | +++ | ++ |
| 1.8% phenoxyethanol | | +++ | + | M | E |

Legend: 8 = very substantial growth
++++ and +++ and ++ and + and M and E = substantial to sporadic growth in decreasing order,
− = no growth
Concentration in use = amount of each formulation in the mixture with water.

As is apparent, furan-2-carboxylic acid is also very effective against Tb in combination with other biocidal alcohols such as phenoxyethanol, even a synergistic increase in effect arising in the case of phenoxyethanol.

EXAMPLE 5

In this example, the efficacy against mycobacteria of carboxylic acids according to the invention was tested in the germ carrier test (cotton) according to DGHM. Again, aqueous solutions of the active ingredients were prepared in each case.

| Carbyoxylic acid | Solvent: Water | | | | |
|---|---|---|---|---|---|
| | Conc. of act. ing. | Contact time | | | |
| | | 15' | 30' | 60' | 120' |
| Furan-2-carboxylic acid | 2% | — | — | — | — |
| Pyridine-2-carbox. acid | 16% | 8 | ++++ | ++++ | + |

Legend: 8 = very substantial growth
++++ and +++ and ++ and + and M and E = substantial to sporadic growth in decreasing order.
— = no growth As was apparent, furan-2-carboxylic acid is significantly more effective than pyridine-2-carboxylic acid even in a substantially lower active ingredient concentration (factor of 8).

The invention has been described in detail with particular reference to preferred embodiments thereof, but it will be understood that variations and modifications can be effected within the spirit and scope of the invention.

We claim:

1. A method of combating mycobacteria comprising the step of treating the mycobacteria with an effective amount of a of furan-2-carboxylic acid, provided that no alkyl sulphonates or alkyl sulphates are present.

2. The method of claim 1 characterized in that furan-2-carboxylic acid is used in the form of one of its salts.

3. The method of claim 1 characterized in that furan-2-carboxylic acid is used in the form of an aqueous an/or alcoholic solution.

4. The method of claim 1 characterized in that the solution has a pH of up to 7.

5. The method of claim 4 characterized in that the solution has a pH of up to 5.

6. The method of claim 5 characterized in that the solution has a pH of up to 4.

7. The method of claim 1 characterized in that furan-2-carboxylic acid is used in a concentration of 0.01 to 8% by wt.

8. The method of claim 7 characterized in that furan-2-carboxylic acid is used in a concentration of 0.1 to 6%, based on the weight of the solution.

9. The method of claim 8 characterized in that furan-2-carboxylic acid is used in a concentration of 0.2 to 4%, based on the weight of the solution.

10. The method of claim 1 characterized in that furan-2-carboxylic acid is present in the form of a liquid concentrate, powder or granular formulation or applied to a support.

* * * * *